US012357326B2

United States Patent
Irving et al.

(10) Patent No.: US 12,357,326 B2
(45) Date of Patent: Jul. 15, 2025

(54) COMBINATION DEPTHSINK INSTRUMENT

(71) Applicant: WRIGHT MEDICAL TECHNOLOGY, INC., Memphis, TN (US)

(72) Inventors: Scott Mitchell Irving, Long Grove, IL (US); Lewis Pearce Branthover, Memphis, TN (US); Nathan William Erickson, Beaverdam, UT (US); Zachary Charles Christensen, Wellsville, UT (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 383 days.

(21) Appl. No.: 17/814,299

(22) Filed: Jul. 22, 2022

(65) Prior Publication Data

US 2023/0081888 A1  Mar. 16, 2023

Related U.S. Application Data

(60) Provisional application No. 63/244,340, filed on Sep. 15, 2021.

(51) Int. Cl.
*A61B 17/17* (2006.01)
*A61B 17/00* (2006.01)
(Continued)

(52) U.S. Cl.
CPC ............ *A61B 17/17* (2013.01); *A61B 90/06* (2016.02); *A61B 2017/00424* (2013.01);
(Continued)

(58) Field of Classification Search
CPC ... A61B 17/17; A61B 90/06; A61B 2090/061; A61B 2090/062; A61B 2017/00424; A61B 2017/564
See application file for complete search history.

(56) References Cited

U.S. PATENT DOCUMENTS

2012/0016373 A1 * 1/2012 Impellizzeri ....... A61B 17/8897
606/104
2016/0278789 A1 * 9/2016 Garvey .................. B65D 71/40

FOREIGN PATENT DOCUMENTS

EP          2398404           10/2016
WO     WO-2015017681 A2 *  2/2015  ......... A61B 17/1728

OTHER PUBLICATIONS

Stryker, Asnis Micro, Cannulated Screw System, Xpress Operative Technique, May 2016.
(Continued)

*Primary Examiner* — Kevin T Truong
*Assistant Examiner* — Diana Jones
(74) *Attorney, Agent, or Firm* — DUANE MORRIS LLP

(57) ABSTRACT

In various embodiments, a surgical instrument, systems including the surgical instrument, and methods of use of the surgical instrument are disclosed. The surgical instrument includes a handle body extending from a proximal end to a distal end substantially along a longitudinal axis. The handle body defines a first channel sized and configured to receive a guide element therein. A plurality of indicators are formed on the handle body. Each of the plurality of indicators correspond to a size of one of a plurality of fixation elements sized and configured for insertion into a bone. A countersink element is coupled to a distal end of the body. The countersink element defines a second channel sized and configured to receive the guide element therethrough that is circumferentially located with and coupled to the first channel. The countersink element includes a head sized and configured to form a countersink in the bone.

18 Claims, 9 Drawing Sheets

(51) Int. Cl.
*A61B 17/56* (2006.01)
*A61B 90/00* (2016.01)

(52) U.S. Cl.
CPC ... *A61B 2017/564* (2013.01); *A61B 2090/061* (2016.02); *A61B 2090/062* (2016.02); *A61B 2090/0807* (2016.02)

(56) References Cited

OTHER PUBLICATIONS

Dart-Fire, Small Screw System, Surgical Technique, Wright Medical Technology, Oct. 5, 2016.
Stryker, Asnis Micro Xpress, Sterile Instrument Solution, May 2016.

* cited by examiner

COMBINATION DEPTHSINK INSTRUMENT

CROSS-REFERENCE TO RELATED APPLICATION

This application claims priority under 35 U.S.C. § 119(e) to U.S. Provisional Application No. 63/244,340, filed on Sep. 15, 2021, the entire contents of which are incorporated herein by reference.

BACKGROUND

During surgery, such as foot surgery, it may be necessary to fix a position of a first bone fragment and a second bone fragment. For example, in some instances, an osteotomy is formed in a bone to correct one or more defects. After forming the osteotomy, a first fragment of the bone and a second fragment of a bone are positioned to correct the defect and are fixed in place using one or more fixation elements. In other instances, one or more bone fragments are formed as a result of an injury and/or medical procedure.

Current systems rely on the use of multiple instruments to determine a length, or depth, of a fixation element to be inserted and to form a countersink in one or more bone portions sized and configured to receive a head of a fixation element. Formation of a countersink after removal of a depth gauge may result in over-drilling of the countersink such that the previously selected fixation element is oversized or undersized for the actual application.

SUMMARY

In various embodiments, a surgical instrument is provided that includes a handle body extending from a proximal end to a distal end substantially along a longitudinal axis. The handle body defines a first channel extending from the distal end in a proximal direction. The first channel is sized and configured to receive a guide element. A plurality of indicators are formed on the handle body. Each of the plurality of indicators corresponds to a size of one of a plurality of fixation elements sized and configured for insertion into a bone. A countersink element is coupled to a distal end of the body. The countersink element defines a second channel sized and configured to receive the guide element. The second channel is circumferentially located with and coupled to the first channel. The countersink element includes a head sized and configured to form a countersink in the bone.

In various embodiments, a kit is disclosed. The kit includes a surgical instrument, a guide element, and a plurality of fixation elements. The surgical instrument includes a handle body extending from a proximal end to a distal end substantially along a longitudinal axis. The handle body defines a first channel extending from the distal end in a proximal direction. A plurality of indicators are formed on the handle body and a countersink element is coupled to a distal end of the body. The countersink element defines a second channel circumferentially located with and coupled to the first channel and includes a head sized and configured to form a countersink in the bone. The guide element is sized and configured to be inserted through the first channel and the second channel. The plurality of fixation elements each have a first dimension that is different. Each of the plurality of indicators of the surgical instrument correspond to the first dimension of one of the plurality of fixation elements.

In various embodiments, a method for inserting a fixation element is provided that includes a steps of inserting a guide element into a bone at a predetermined location and coupling a surgical instrument to the guide element. The surgical instrument includes a handle body extending from a proximal end to a distal end substantially along a longitudinal axis. The handle body defines a first channel extending from the distal end in a proximal direction that is sized and configured to receive a guide element therein. A countersink element is coupled to a distal end of the body and defines a second channel sized and configured to receive the guide element therethrough. The second channel is circumferentially located with and, coupled to, the first channel. The countersink element includes a head sized and configured to form a countersink in the bone. The method further includes a step of determining a length of a fixation element to be inserted into the bone based on a position of the guide element with respect to a plurality of indicators formed on the handle body. Each of the plurality of indicators correspond to a size of one of a plurality of fixation elements sized and configured for insertion into a bone. The fixation element is selected from the plurality of fixation elements. The method further includes steps of forming a countersink in the bone by driving the head of the countersink element to a predetermined depth within the bone, removing the surgical instrument from the guide element, and inserting the fixation element into the bone.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
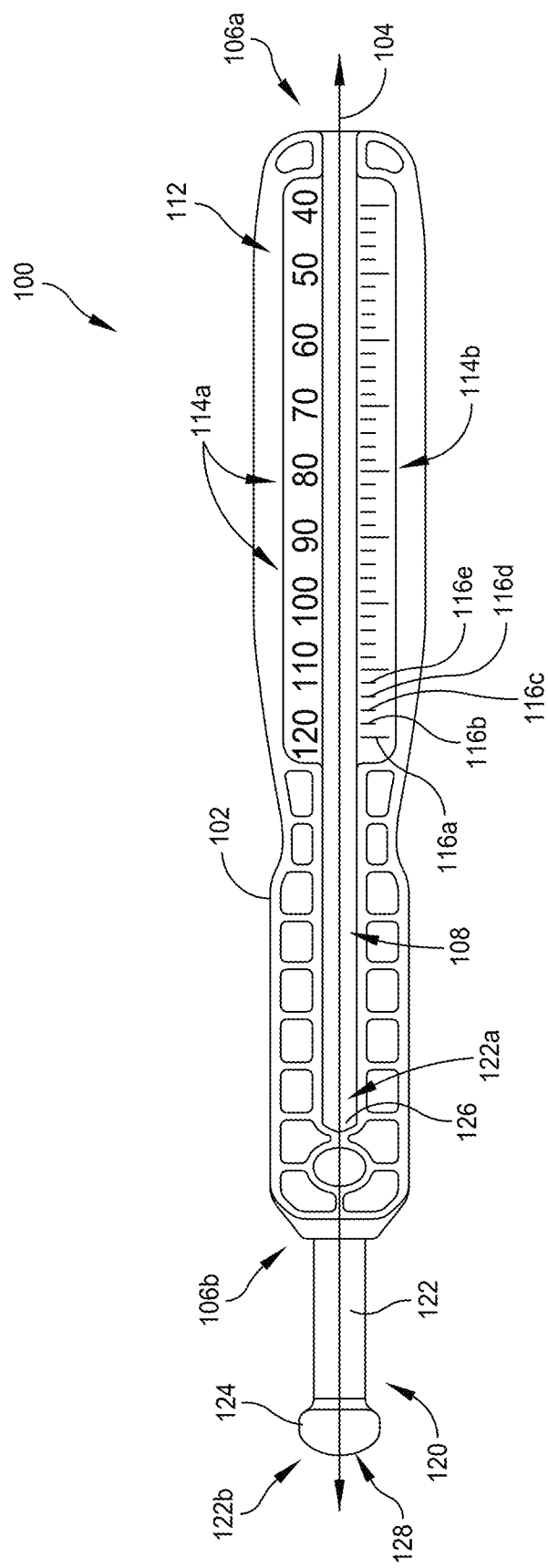
FIG. 1 illustrates one example of surgical instrument, in accordance with some embodiments.

The description of the preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In this description, relative terms such as "horizontal," "vertical," "up," "down," "top," "bottom," as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both moveable or rigid attachments or relationships, unless expressly described otherwise. The term "operatively coupled" is such an attachment, coupling, or connection that allows the pertinent structures to operate as intended by virtue of that relationship.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

In various embodiments, a surgical instrument, which may be referred to herein as a "depthsink" instrument, is configured to provide both measurement related to a fixation element and formation of a countersink for a fixation element. The surgical instrument includes one or more measurement structures or features configured to provide a measurement related to a length of a fixation element that is to be inserted into an anatomical structure. The surgical instrument further includes a distal head configured to form a countersink in a portion of the anatomical structure. The countersink may be formed prior to, simultaneous with, and/or after determining the length of a fixation element to be inserted. Various systems including the depthsink instrument and methods of using the depthsink instrument are also disclosed.

FIG. 1 illustrates one embodiment of surgical instrument 100, in accordance with some embodiments. The surgical instrument 100 includes a handle body 102 extending substantially along a longitudinal axis 104 from a proximal end 106a to a distal end 106b. The handle body 102 may be formed of any suitable material, such as, for example, a plastic material, a resin material, a rubber material, a metal material, any other suitable material, and/or any combination thereof. In some embodiments, the handle body 102 defines a channel 108 extending substantially along the longitudinal axis 104. The channel 108 is sized and configured to receive a guide element, such as a k-wire, therethrough. In the illustrated embodiment, the channel 108 is centered in the handle body 102, although it will be appreciated that the channel 108 may be offset and/or angled with respect to the handle body 102. The channel 108 includes a proximal opening 110 at a proximal end 106a of the handle body 102. The proximal opening 110 is sized and configured to allow a fixation element, such as a k-wire, to pass through the proximal end 106a of the handle body 102.

In some embodiments, the handle body 102 defines a measurement indicator 112 including one or more structures or features sized and configured to provide a measurement that corresponds to one or more dimensions of fixation element. In the illustrated embodiment, the measurement indicator 112 is configured to provide a measurement corresponding to a length of a fixation element to be inserted into an anatomical structure, although it will be appreciated that other dimensions of a fixation element (or other surgical element) may be indicated. In some embodiments, the measurement indicator 112 includes a plurality of indicators formed on a surface of the handle body 102. In the illustrated embodiment, the plurality of indicators include both numerical indicators 114a and hash marks 114b, although it will be appreciated that any suitable indicator may be used. The numerical indicators 114a may indicate any suitable numerical range corresponding to a measured dimension of a fixation element. For example, in the illustrated embodiment, the numerical indicators 114a range from 40-120 ascending from a proximal direction to a distal direction (or, alternatively, descending from a distal direction to a proximal direction). The hash mark indicators 114b may correspond to various increments and may include larger and/or smaller hash marks. For example, in the illustrated embodiment, the hash mark indicators 114b are divided into increments of five, with the first hash mark 116a in each set being larger (e.g., having a longer longitudinal length and/or greater width) than the other four marks 116b-116e.

In some embodiments, the numerical indicators 114a may correspond directly to a physical dimension of a fixation device, such as, for example, a length of a fixation device. For example, in the illustrated embodiment, the numerical indicators 114a range from 40-120 ascending from a proximal direction to a distal direction, which correspond to a length, in millimeters, of a fixation screw to be inserted into an anatomical structure, such as a bone. As discussed in greater detail with respect to FIG. 3, when a guide element is coupled to a bone and inserted into the channel 108 defined by the handle body 102, the position of a distal end of the guide element corresponds to a length, in millimeters, of a fixation device to be inserted into the bone. In other embodiments, the numerical indicators 114a may correspond to numerical designations for various sizes of fixation elements, for example, size 1, 2, 3, etc. It will be appreciated that any suitable numerical system with corresponding numerical indicators 114a may be used to determine a corresponding size of a fixation element to be used.

In some embodiments, the hash mark indicators 114b may correspond to subdivisions of the numerical indicators 114a. For example, in the illustrated embodiment, each of the first hash marks 116a correspond to the location of a numerical indicator 114a. The second hash marks 116b-116e correspond to a subdivision of the numerical indicators in the amount of a 2 millimeter increment. Although specific embodiments are illustrated and discussed herein, it will be appreciated that the hash mark indicators 114b may correspond to any suitable subdivision of the numerical indictors 114a.

Although embodiments are illustrated having a first set of indicators, e.g., numerical indicators 114a, and a second set of indicators, e.g., hash mark indicators 114b, that correspond, it will be appreciated that multiple sets of indicators having different and/or unrelated measurements may be provided. For example, in some embodiments, a first set of indicators may correspond to a length of a first fixation device to be inserted into a bone and a second set of indicators may correspond to a length of a second fixation device to be inserted into a bone. Other examples may include first indicators corresponding to a length of a fixation device and second indicators corresponding to a size of an additional surgical element, such as a surgical plate. It will be appreciated that any suitable combination of indicators may be provided on the surgical instrument 100.

The indicators 114 may extend over any suitable portion of the handle body 102. For example, in the illustrated embodiment, the indicators 114 are provided from about a mid-point of the handle body 102 to a proximal end 106a of the handle body 102. The location of the indicators 114 on the handle body 102 may be selected based on one or more dimensions of the surgical instrument 100, such as, for example, a length of the handle body 102 on the longitudinal axis 104, a length of a countersink element 120 coupled the handle body 102 (discussed in greater detail below), and/or any other suitable dimension.

In some embodiments, the surgical instrument 100 includes a countersink element 120 coupled to a distal end 106b of the handle body 102. The countersink element 120 includes a shaft 122, a head element 124, and a retention element 126. The shaft 122 extends substantially along a longitudinal axis from a proximal end 122a to a distal end 122b. The head element 124 is formed at and/or coupled to the distal end 122b of the shaft 122 and the retention element 126 is formed at and/or coupled to the proximal end 122a of the shaft 122. The countersink element 120 defines a channel 128 extending from the proximal end 122a to the distal end 122b of the countersink element 120. The channel formed concentrically in the countersink element 120 and extends through each of the shaft 122, the head element 124, and the retention element 126. The channel 128 is sized and configured to receive a guide element, such as a k-wire. In some embodiments, a diameter of the channel 128 in the countersink element 120 is equal to or less than the diameter of the channel 108 formed in the handle body 102.

In some embodiments, the countersink element 120 is coupled to the handle body 102 during formation of the handle body 102. For example, in some embodiments, the handle body 102 is overmolded for formed integrally with the countersink element 120. As another example, in some embodiments, the handle body 102 includes a two-part body that is connected together using a snap-fit, fastener, glue, etc. The countersink element 120 is disposed between the two halves of the handle body 102 prior to the two halves being connected. Although specific embodiments are discussed herein, it will be appreciated that any suitable method of connecting the countersink element 120 to the handle body 102 may be used.

The countersink element 120 includes a head element 124 sized and configured to form a countersink in an anatomical structure, such as a bone. The head element 124 may be configured to form a countersink through any suitable mechanism, such as cutting, reaming, impacting, and/or other method of forming a countersink. In the illustrated embodiment, the head element 124 includes an element configured to apply an impacting force. The proximal end 106a of the handle body 102 may include an impaction surface configured to receive a force applied, for example, by a hammer or other tool. The force is transferred to the countersink element 120, and specifically the head element 124, which is driven into the anatomical structure to form a countersink. Other methods, such as drilling or reaming, may alternatively or additional be applied by a head element 124.

In some embodiments, the head element 124 is configured to form a countersink having a predetermined size and depth corresponding to a head portion of a fixation element to be coupled to the anatomical structure. For example, in some embodiments, the head element 124 is a circumferential element having a diameter equal to or greater than a circumference of a head portion of a fixation element to be inserted into the anatomical structure and the head element 124 has a height (or depth) equal to or greater than the height (or depth) of the circumference of the head portion of the fixation element. In some embodiments, the head element 124 is configured to form a countersink sufficient to receive the entirety of a head portion of a fixation element to be disposed below a surface of the anatomical structure after insertion, although it will be appreciated that the countersink may be sized only to receive a portion of the head portion therein. In some embodiments, the shaft 122 of the countersink element 120 defines a first cross-sectional diameter and the head element 124 defines a second cross-sectional diameter that is greater than the first diameter of the shaft 122.

Figure 2:
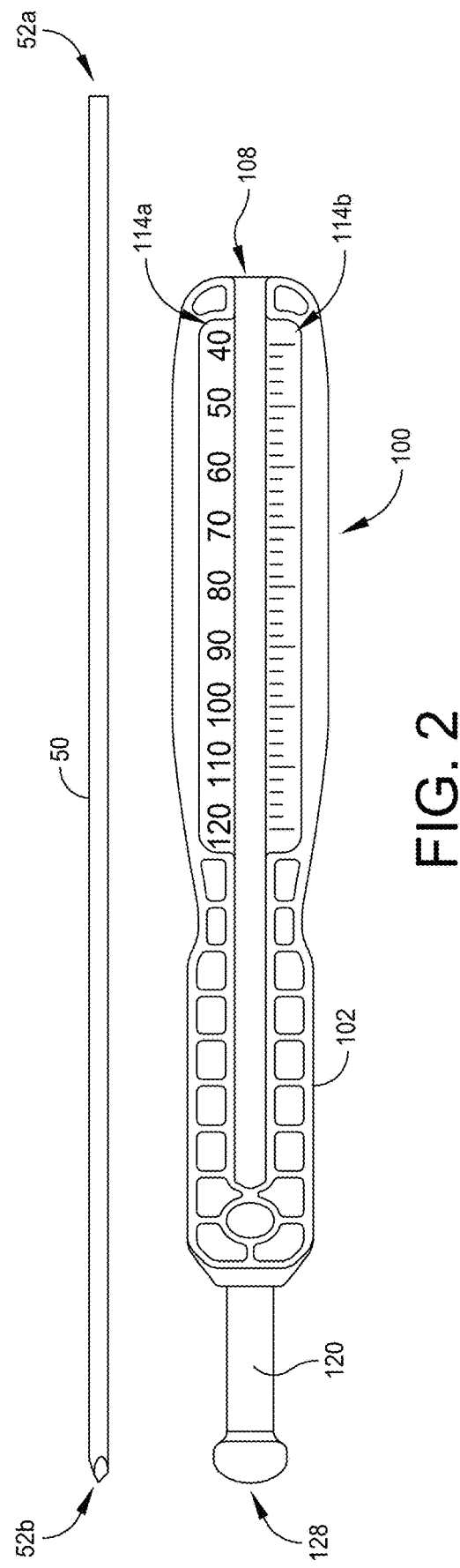
FIG. 2 illustrates the surgical instrument of FIG. 1 and a corresponding guide element, in accordance with some embodiments.
Figure 3:
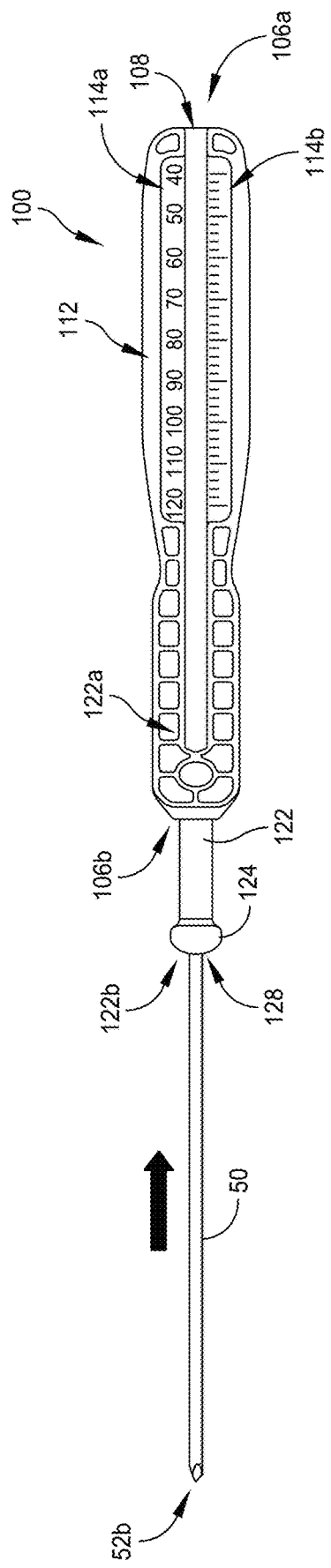
FIG. 3 illustrates the surgical instrument of FIG. 1 slideably coupled to a guide element, in accordance with some embodiments.

FIG. 2 illustrates the surgical instrument 100 of FIG. 1 and an associated guide element 50 that includes an elongate structure sized and configured to be received through the channels 128, 108 defined by the countersink element 120 and the handle body 102, respectively. The guide element 50 can include any suitable guide element, such as a k-wire (as shown), a pin, etc. The guide element 50 may be inserted at a predetermined anatomical location using one or more insertion guides, as known in the art. FIG. 3 illustrates the surgical instrument 100 of FIG. 1 being slideably engaged with the associated guide element 50, in accordance with some embodiments. More particularly, the guide element 50 is received within the distal end of the channel 128 defined in the countersink element 120. The guide element 50 is inserted through the channel 128 into the channel 108 defined in the handle body 102. As discussed in greater detail below, the guide element 50 is inserted into an anatomical structure, such as a bone, prior to coupling the surgical instrument 100 to the guide element 50. In use, the head element 124 of the countersink element 120 will contact a surface of the anatomical structure after insertion of the guide element 50 into the channels 108, 128. When the head element 124 is abutted against a surface of the anatomical structure, the proximal end 52a of the guide element 50 will be positioned at or near one or more of the indicators 114 formed on the handle body 102.

In some embodiments, a location of a portion of the guide element 50 with respect to the indicators 114, such as a location of the proximal end 52a of the guide element 50, corresponds to a dimension of a fixation element to be coupled to the anatomical structure. For example, in the illustrated embodiment, the location of the proximal end 52a of the guide element 50 corresponds to a length measurement of a fixation element, such as a screw, to be inserted into the anatomical structure. The indicators 114 may be configured to provide a measurement prior to and/or after formation of a countersink by the countersink element 120 in the anatomical structure. Although embodiments are discussed herein using a proximal end 52a of a guide element as a measurement location, it will be appreciated that any suitable portion of a guide element 50 may be used. For example, in some embodiments, one or more marks may be formed on the guide element 50 and used for reference with respect to the indicators 114 formed on the handle body 102.

Figure 4:
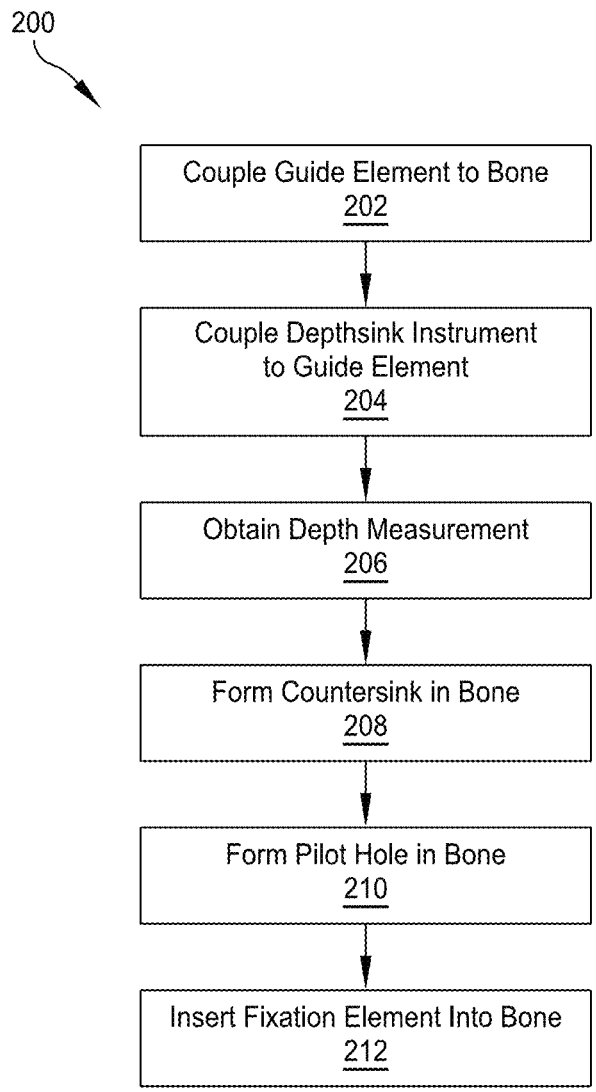
FIG. 4 is a flowchart illustrating a method of inserting a fixation element into one or more bones, in accordance with some embodiments.
Figure 5:
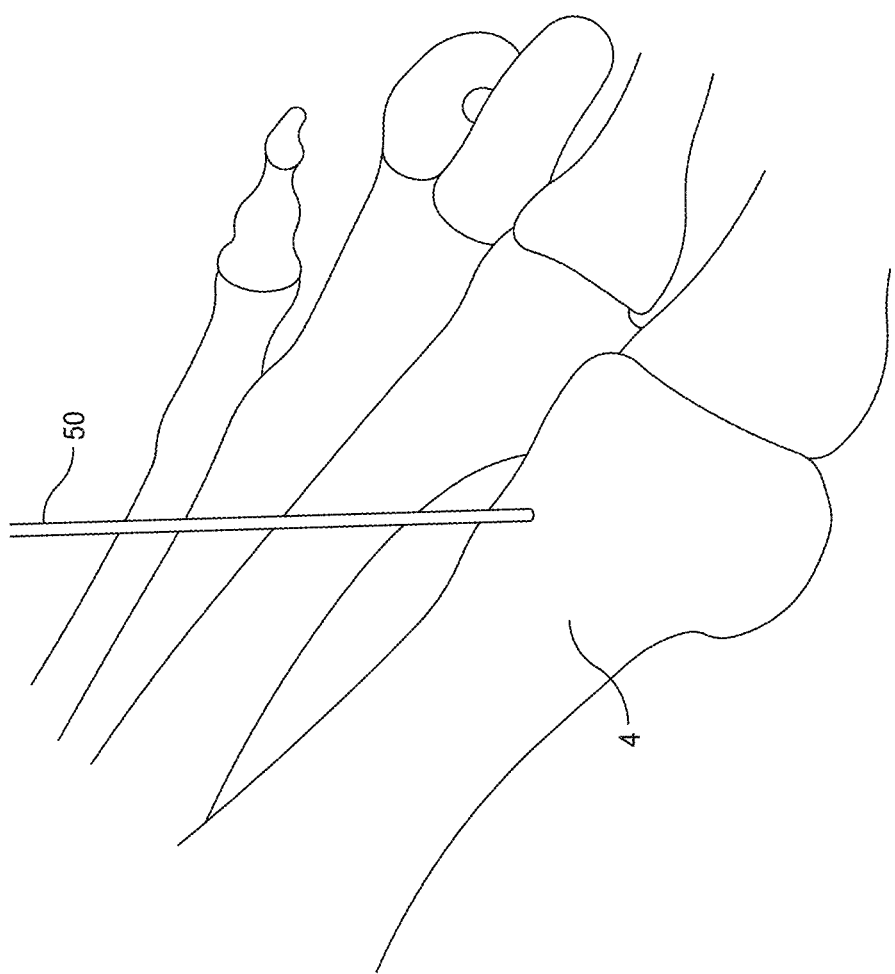
FIG. 5 illustrates a surgical site having a guide element coupled thereto, in accordance with some embodiments.

FIG. 4 is a flowchart illustrating a method 200 for inserting a fixation device into a bone, in accordance with some embodiments. FIGS. 5-9 illustrate various steps of the method 200, in accordance with various embodiments. The method 200 of inserting a fixation device into a bone is discussed with reference to FIGS. 4-9. At step 202, a guide element 50 is inserted into at least one bone 4 or bone fragment in a predetermined position, as illustrated in FIG. 5. For example, in some embodiments, the guide element 50 is inserted using one or more targeting devices (now shown) configured to position the guide element 50 at a predetermined position on the bone 4. The guide element 50 may be any suitable guide element, such as a k-wire, and may be inserted using any suitable mechanism, such as a tool, hand insertion, etc. In some embodiments, a pilot hole may be formed prior to insertion of the guide element 50, although it will be appreciated that the guide element may be "self-drilling" such that a pilot hole need not be formed prior to insertion. It will be appreciated that the guide element 50 may be inserted into multiple bones and/or bone fragments.

Figure 6:
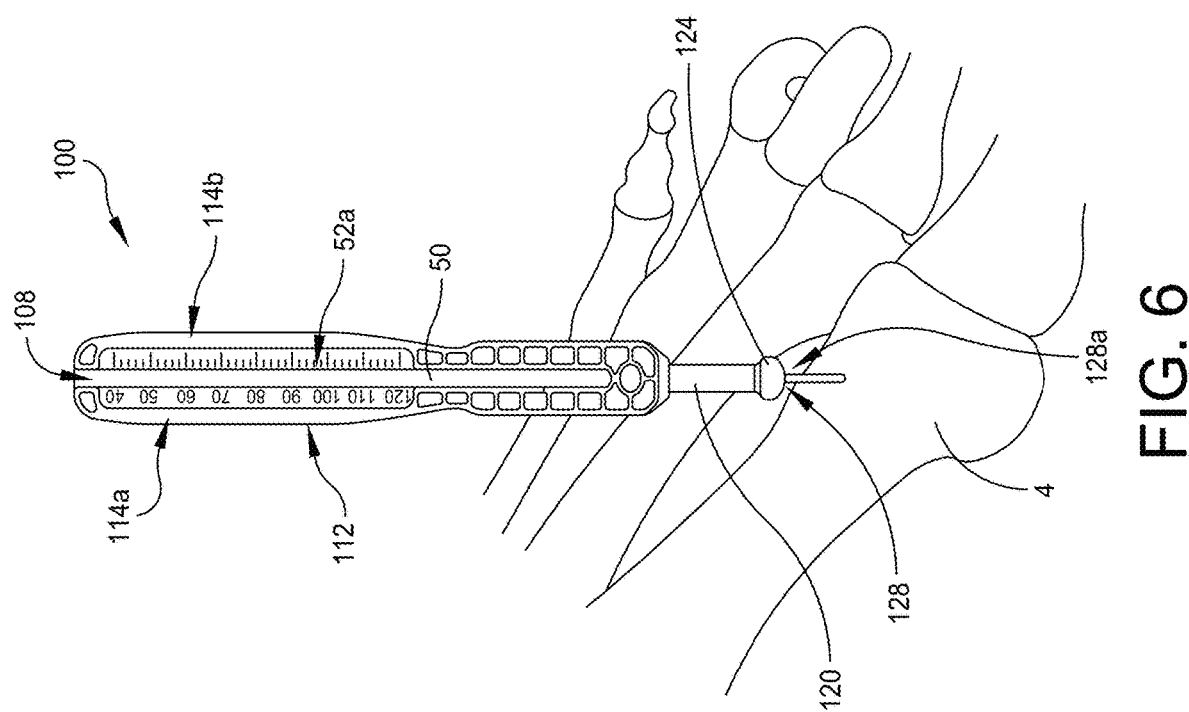
FIG. 6 illustrates the surgical site of FIG. 5 having a surgical instrument slideably coupled to the guide element, in accordance with some embodiments.

At step 204, a depthsink instrument configured to provide a depth measurement and create a countersink in the bone 4, such as the surgical instrument 100 discussed above, is coupled to the guide element 50, as illustrated in FIG. 6. The surgical instrument 100 may be coupled to the guide element 50 by inserting a proximal end 52a of the guide element 50 into the distal end 128a of the channel 128 formed in the countersink element 120. The guide element 50 is inserted further into the channel 128 and the channel 108 until the head element 124 of the countersink element 50 is brought into surface contact with the bone 4.

At step 206, a depth measurement is obtained based on one or more of the plurality of indicators 114. For example, in the illustrated embodiment, the proximal end 52a of the guide element 50 is positioned adjacent to one or more of the plurality of indicators 114 when the head element 124 is positioned adjacent to the bone 4. The one of the plurality of indicators 114 corresponds to a size of a fixation element to be inserted into the bone. For example, in some embodiments, a numerical indicator 114a may indicate a length of a screw in millimeters, although it will be appreciated that any suitable indicators may be used to denote a dimension of a fixation element to be inserted into the bone.

Figure 7:
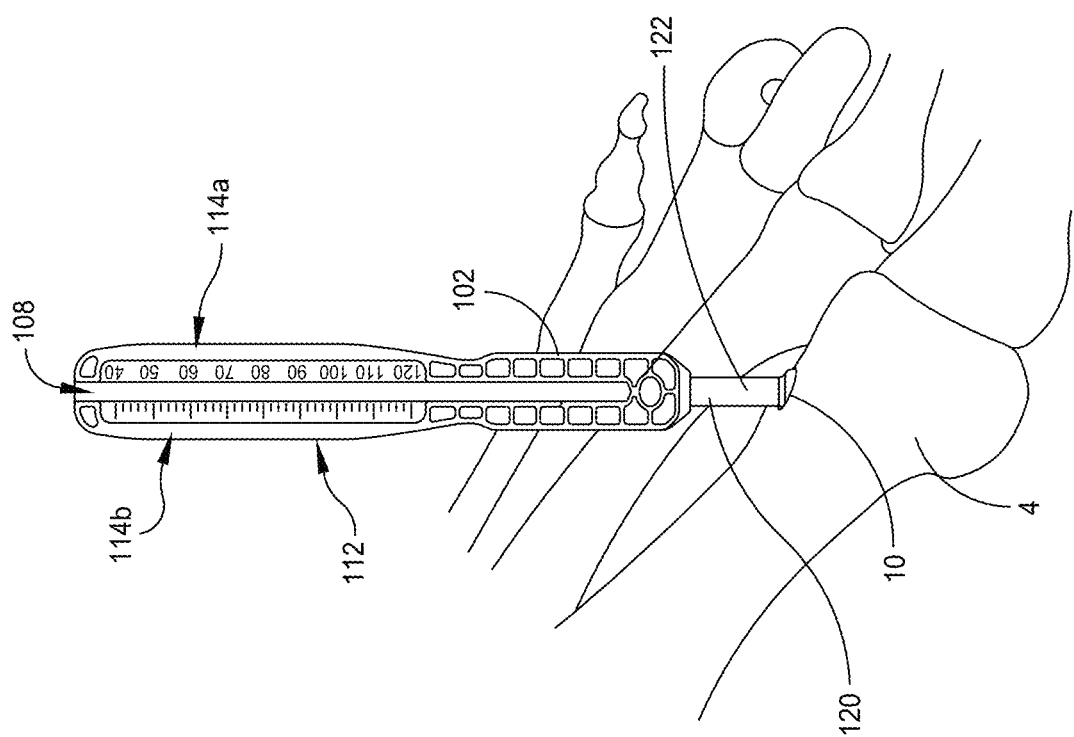
FIG. 7 illustrates the surgical site of FIG. 6 after insertion of the head portion of the surgical instrument to form a countersink, in accordance with some embodiments.
Figure 8:
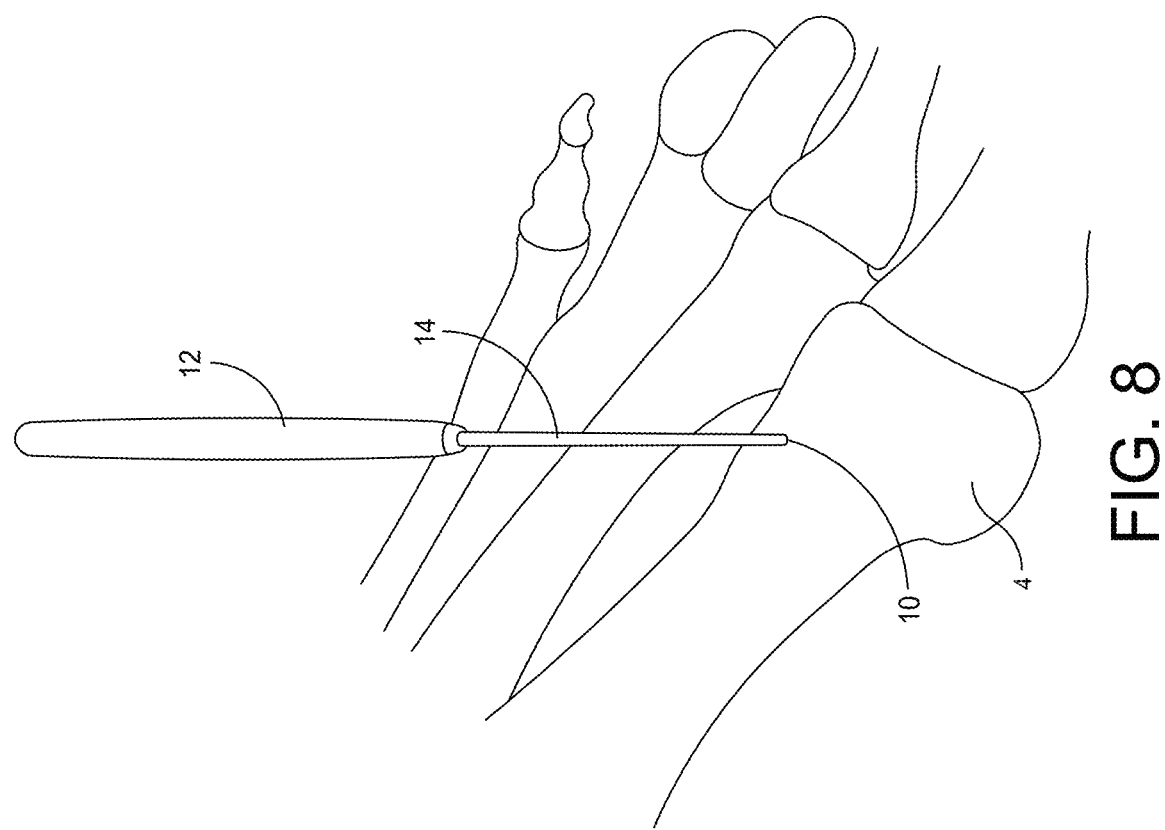
FIG. 8 illustrates the surgical site of FIG. 7, having a drill coupled to the guide element, in accordance with some embodiments.
Figure 9:
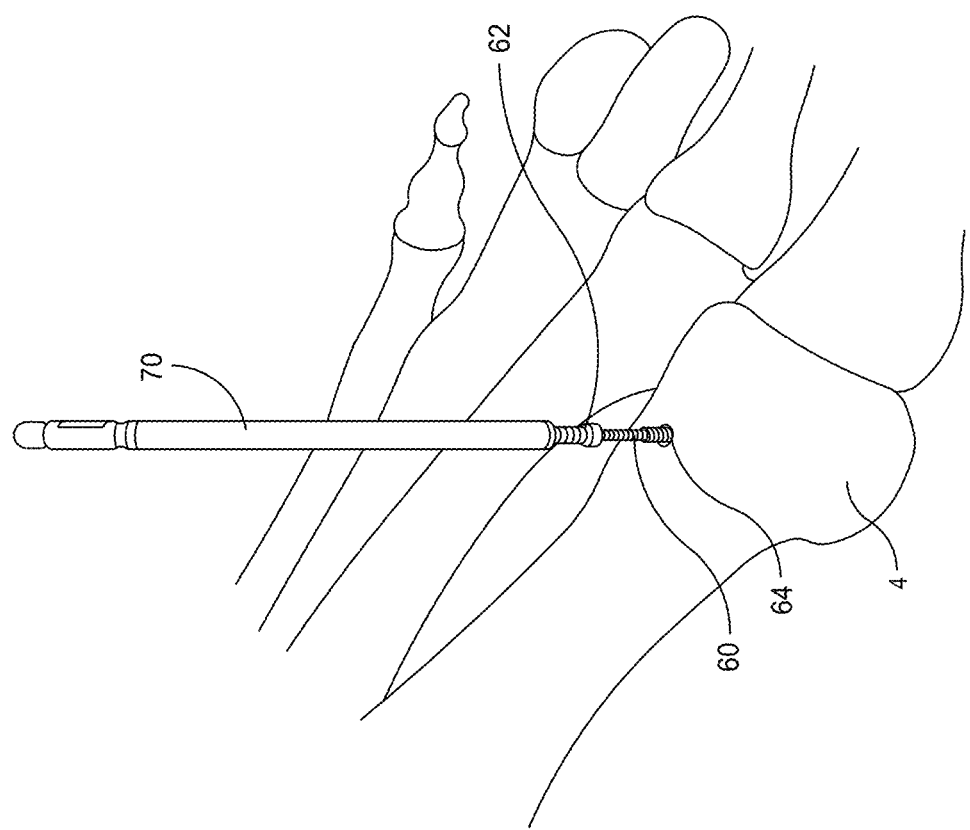
FIG. 9 illustrates the surgical site of FIG. 8, having a cannulated screw and driver coupled to the guide element, in accordance with some embodiments.

At step 208, a countersink 10 is formed in the bone 4, as illustrated in FIG. 7. The countersink 10 is formed by the head element 124 of the countersink element 120. The head element 124 may be driven into the bone, for example, by an impaction force, rotational force, etc. In some embodiments, the countersink 10 is sized and configured to receive a head portion of a fixation element, such as a screw 60, therein (see FIG. 9). Although step 208 is illustrated and discussed as occurring after step 206, it will be appreciated that the countersink 10 may be formed prior to measuring the depth (or other dimension) of a fixation element to be inserted into the bone 4.

At step 210, a pilot hole for the fixation element is formed in the bone 4. The pilot hole may be formed using any suitable mechanism, such as, for example, a drill 12 including a drill bit 14. The drill bit 14 may be inserted over the guide element 50 and/or inserted after removal of the guide element 50. The drill bit 14 may be selected based on the size of the fixation element identified by the depthsink instrument at step 206. After forming the pilot hole, the drill 12 and the drill bit 14 are removed.

At step 212, a fixation element is inserted into the bone 4. For example, in the illustrated embodiment, a screw 60 is inserted into the bone 4 by a driver 70. The screw 60 and/or the driver 70 may be inserted over the guide element 50. The driver 70 drives the screw 60 into the pilot hole formed at step 210 until the head 62 of the screw 60 is driven into the countersink 10 formed in the bone. In some embodiments, the screw 60 is driven into the bone 4 such that the head 62 is positioned below a surface of the bone 4, although it will be appreciated that a portion of the head 62 may extend above the surface of the bone 4.

The fixation element, such as screw 60, includes at least one dimension that corresponds to the depth measurement performed at step 206. For example, in some embodiments, the fixation element is selected from a plurality of fixation elements each having at least one varied dimension. In the illustrated embodiment, the screw 60 is selected from a plurality of screws each having a different length, although it will be appreciated that additional and/or alternative dimensions may be measured and/or varied. The screw 60 has a first length corresponding to the depth measurement obtained at step 206, such as, for example, having a length, in millimeters, equal to the numerical indicator positioned adjacent to a predetermined portion of the guide element 50 when the guide element 50 is inserted into the channel 108.

In various embodiments, a surgical instrument includes a handle body extending from a proximal end to a distal end substantially on a longitudinal axis. The handle body defines a first channel extending from the distal end in a proximal direction. The first channel is sized and configured to receive a guide element therein. A plurality of indicators are formed on the handle body. Each of the plurality of indicators corresponds to a size of one of a plurality of fixation elements sized and configured for insertion into a bone. A countersink element is coupled to a distal end of the body. The countersink element defines a second channel sized and configured to receive the guide element. The second channel is circumferentially located with and coupled to the first channel. The countersink element includes a head sized and configured to form a countersink in the bone.

In some embodiments, the head of the countersink instrument comprises an impaction head, while in other embodiments the head of the countersink instrument is configured to form a countersink at least partially through rotation of the countersink element.

In some embodiments, the plurality of indicators comprise numerical indicators.

In some embodiments, a diameter of the head of the countersink element is equal to or greater than a diameter of a head of each of the plurality of fixation elements.

In some embodiments, a depth of the head of the countersink element is equal to or greater than a depth of a head of each of the plurality of fixation elements.

In some embodiments, the first channel has a first diameter and the second channel has a second diameter and the second diameter is less than the first diameter.

In various embodiments, a kit includes a surgical instrument, a guide element, and a plurality of fixation elements. The surgical instrument includes a handle body extending from a proximal end to a distal end substantially along a longitudinal axis. The handle body defines a first channel extending from the distal end in a proximal direction. A plurality of indicators are formed on the handle body and a countersink element is coupled to a distal end of the body. The countersink element defines a second channel circumferentially located with and coupled to the first channel and includes a head sized and configured to form a countersink in the bone. The guide element is sized and configured to be inserted through the first channel and the second channel. The plurality of fixation elements each have a first dimension that is different. Each of the plurality of indicators of the surgical instrument correspond to the first dimension of one of the plurality of fixation elements.

In some embodiments, the head of the countersink instrument comprises an impaction head, while in other embodiments the head of the countersink instrument is configured to form a countersink at least partially through rotation of the countersink element.

In some embodiments, the plurality of indicators comprise numerical indicators.

In some embodiments, a diameter of the head of the countersink element is equal to or greater than a diameter of a head of each of the plurality of fixation elements.

In some embodiments, a depth of the head of the countersink element is equal to or greater than a depth of a head of each of the plurality of fixation elements.

In some embodiments, the first channel has a first diameter and the second channel has a second diameter that is less than the first diameter.

In various embodiments, a method of inserting a fixation element is disclosed. The method includes a steps of inserting a guide element into a bone at a predetermined location and coupling a surgical instrument to the guide element. The surgical instrument includes a handle body extending from a proximal end to a distal end substantially along a longitudinal axis. The handle body defines a first channel extending from the distal end in a proximal direction that is sized and configured to receive a guide element therein. A countersink element is coupled to a distal end of the body and defines a second channel sized and configured to receive the guide element therethrough. The second channel is circumferentially located with and coupled to the first channel. The countersink element includes a head sized and configured to form a countersink in the bone. The method further includes a step of determining a length of a fixation element to be inserted into the bone based on a position of the guide element with respect to a plurality of indicators formed on the handle body. Each of the plurality of indicators correspond to a size of one of a plurality of fixation elements sized and configured for insertion into a bone. The fixation element is selected from the plurality of fixation elements. The method further includes steps of forming a countersink in the bone by driving the head of the countersink element to a predetermined depth within the bone, removing the surgical instrument from the guide element, and inserting the fixation element into the bone.

In some embodiments, determining a length of a fixation element comprises determining a position of a proximal end of the guide element with respect to the plurality of indicators.

In some embodiments, the countersink formed in the bone is sized and configured to receive a head portion of the fixation element therein.

In some embodiments, the countersink is formed in the bone at least partially through impaction of the surgical instrument.

In some embodiments, the plurality of indicators comprise numerical indicators.

In some embodiments, the length of the fixation element is determined after forming the countersink in the bone.

Although the subject matter has been described in terms of exemplary embodiments, it is not limited thereto. Rather, the appended claims should be construed broadly, to include other variants and embodiments, which may be made by those skilled in the art.

What is claimed is:

1. A surgical instrument, comprising
a handle body extending from a proximal end to a distal end substantially along a longitudinal axis, wherein the handle body defines a first channel extending from the distal end in a proximal direction, wherein the first channel has a first diameter sized and configured to receive a guide element therein;
a plurality of indicators formed on the handle body, wherein each of the plurality of indicators correspond to a size of one of a plurality of fixation elements sized and configured for insertion into a bone;
a countersink element coupled to the distal end of the handle body, the countersink element defining a second channel sized having a second diameter less than the first diameter configured to receive the guide element therethrough, wherein the second channel is circumferentially located with and coupled to the first channel, and wherein the countersink element includes a head sized and configured to form a countersink in the bone.

2. The surgical instrument of claim 1, wherein the head of the countersink element comprises an impaction head.

3. The surgical instrument of claim 1, wherein the head of the countersink element is configured to form the countersink at least partially through rotation of the countersink element.

4. The surgical instrument of claim 1, wherein the plurality of indicators comprise numerical indicators.

5. The surgical instrument of claim 1, wherein a diameter of the head of the countersink element is equal to or greater than a diameter of a head of each of the plurality of fixation elements.

6. The surgical instrument of claim 1, wherein a depth of the head of the countersink element is equal to or greater than a depth of a head of each of the plurality of fixation elements.

7. A kit, comprising:
A surgical instrument, comprising
a handle body extending from a proximal end to a distal end substantially along a longitudinal axis, wherein the handle body defines a first channel having a first diameter and extending from the distal end in a proximal direction;
a plurality of indicators formed on the handle body;
a countersink element coupled to the distal end of the handle body, the countersink element defining a second channel having a second diameter less than the first diameter that is circumferentially located with and coupled to the first channel, and wherein the countersink element includes a head sized and configured to form a countersink in a bone;
a guide element sized and configured to be inserted through the first channel and the second channel; and
a plurality of fixation elements each having a first dimension that is different, wherein each of the plurality of indicators of the surgical instrument correspond to the first dimension of one of the plurality of fixation elements.

8. The kit of claim 7, wherein the head of the countersink element comprises an impaction head.

9. The kit of claim 7, wherein the head of the countersink element is configured to form the countersink at least partially through rotation of the countersink element.

10. The kit of claim 7, wherein the plurality of indicators comprise numerical indicators.

11. The kit of claim 7, wherein a diameter of the head of the countersink element is equal to or greater than a diameter of a head of each of the plurality of fixation elements.

12. The kit of claim 7, wherein a depth of the head of the countersink element is equal to or greater than a depth of a head of each of the plurality of fixation elements.

13. A method of inserting a fixation element, comprising:
inserting a guide element into a bone at a predetermined location;
coupling a surgical instrument to the guide element, wherein the surgical instrument comprises:
- a handle body extending from a proximal end to a distal end substantially along a longitudinal axis, wherein the handle body defines a first channel extending from the distal end in a proximal direction, wherein the first channel has a first diameter sized and configured to receive the guide element therein; and
- a countersink element coupled to the distal end of the handle body, the countersink element defining a second channel having a second diameter less than the first diameter sized and configured to receive the guide element therethrough, wherein the second channel is circumferentially located with and coupled to the first channel, and wherein the countersink element includes a head sized and configured to form a countersink in a bone;

determining a length of the fixation element to be inserted into the bone based on a position of the guide element with respect to a plurality of indicators formed on the handle body, wherein each of the plurality of indicators correspond to a size of one of a plurality of fixation elements sized and configured for insertion into the bone, and wherein the fixation element is selected from the plurality of fixation elements;

forming the countersink in the bone by driving the head of the countersink element to a predetermined depth within the bone;

removing the surgical instrument from the guide element; and inserting the fixation element into the bone.

14. The method of claim 13, wherein determining the length of the fixation element comprises determining a position of a proximal end of the guide element with respect to the plurality of indicators.

15. The method of claim 13, wherein the countersink formed in the bone is sized and configured to receive a head portion of the fixation element therein.

16. The method of claim 13, wherein the countersink is formed in the bone at least partially through impaction of the surgical instrument.

17. The method of claim 13, wherein the plurality of indicators comprise numerical indicators.

18. The method of claim 13, wherein the length of the fixation element is determined after forming the countersink in the bone.

* * * * *